United States Patent
Watkins et al.

(10) Patent No.: US 6,731,383 B2
(45) Date of Patent: May 4, 2004

(54) CONFOCAL 3D INSPECTION SYSTEM AND PROCESS

(75) Inventors: Cory Watkins, Chanhassen, MN (US); Alan Blair, St. Paul, MN (US)

(73) Assignee: August Technology Corp., Bloomington, MN (US)

( * ) Notice: Subject to any disclaimer, the term of this patent is extended or adjusted under 35 U.S.C. 154(b) by 0 days.

(21) Appl. No.: 09/952,537

(22) Filed: Sep. 12, 2001

(65) Prior Publication Data
US 2002/0191178 A1 Dec. 19, 2002

Related U.S. Application Data
(60) Provisional application No. 60/232,443, filed on Sep. 12, 2000.

(51) Int. Cl.[7] .................. G01N 21/00; G01B 11/00; G03B 27/54; G03B 5/04; G03B 26/08
(52) U.S. Cl. .................. 356/237.2; 356/237.1; 356/399; 356/400; 355/67; 359/212; 359/833
(58) Field of Search .................. 356/237.1, 237.2, 356/399–401; 359/212, 833; 250/212; 355/67

(56) References Cited

U.S. PATENT DOCUMENTS

| | | | |
|---|---|---|---|
| 4,719,341 A | | 1/1988 | Hoogenboom ............ 250/203.2 |
| RE32,660 E | * | 5/1988 | Lindow et al. ............ 250/225 |
| 4,802,748 A | | 2/1989 | McCarthy et al. ........... 359/368 |
| 4,930,896 A | * | 6/1990 | Horikawa .................... 356/609 |
| 4,965,442 A | | 10/1990 | Girod et al. ............ 250/201.7 |
| 5,067,805 A | | 11/1991 | Corle et al. .................. 359/235 |
| 5,072,128 A | * | 12/1991 | Hayano et al. ......... 250/559.18 |
| 5,073,018 A | | 12/1991 | Kino et al. .................. 359/368 |
| 5,083,220 A | | 1/1992 | Hill ............................. 359/234 |
| 5,248,876 A | | 9/1993 | Kerstens et al. ............ 250/559 |
| 5,329,358 A | | 7/1994 | Horijon ....................... 356/624 |
| 5,386,317 A | | 1/1995 | Corle et al. ................. 359/386 |
| 5,428,475 A | | 6/1995 | Tanaami et al. ............ 359/368 |
| 5,448,359 A | | 9/1995 | Schick et al. ............... 356/609 |
| 5,594,242 A | | 1/1997 | Konishi et al. ............. 250/234 |
| 5,696,591 A | * | 12/1997 | Bilhorn et al. .............. 356/429 |
| 5,734,497 A | | 3/1998 | Yano, deceased et al. .. 359/368 |
| 5,737,084 A | * | 4/1998 | Ishihara ....................... 356/609 |
| 5,991,040 A | | 11/1999 | Doemens et al. ........... 356/614 |
| 6,108,090 A | * | 8/2000 | Ishihara ....................... 356/601 |
| 6,224,216 B1 | * | 5/2001 | Parker et al. .................. 353/31 |
| 6,224,276 B1 | | 5/2001 | Funayama et al. ........ 400/227.1 |
| 6,288,382 B1 | * | 9/2001 | Ishihara .................... 250/201.3 |
| 6,426,835 B1 | | 7/2002 | Endo et al. .................. 359/388 |

FOREIGN PATENT DOCUMENTS

| | | |
|---|---|---|
| DE | 1 949 117 | 9/1969 |
| EP | 0 615607 | 11/1992 |
| WO | WO 92/14118 | 8/1992 |
| WO | WO 93/11403 | 6/1993 |
| WO | WO 03/008940 | 1/2003 |

OTHER PUBLICATIONS

A copy of PCT International Search Report mailed on Jan. 2, 2003 (7 pages).

* cited by examiner

*Primary Examiner*—Russell Adams
*Assistant Examiner*—Magda Cruz
(74) *Attorney, Agent, or Firm*—John A. Vasuta; Timothy A. Czaja

(57) ABSTRACT

A confocal three dimensional inspection system, and process for use thereof, allows for inspecting of bumps and other three dimensional (3D) features on wafers and other semiconductor substrates. The sensor eliminates out of focus light using a confocal principal to improve depth response. This process and system creates multiple parallel confocal optical paths along a line. The out of focus light is eliminated by placing an aperture at a plane which is a conjugate focal plane to the surface of the sample. The result is that the sensor produces a signal only when the sample surface is in a narrow focal range.

19 Claims, 4 Drawing Sheets

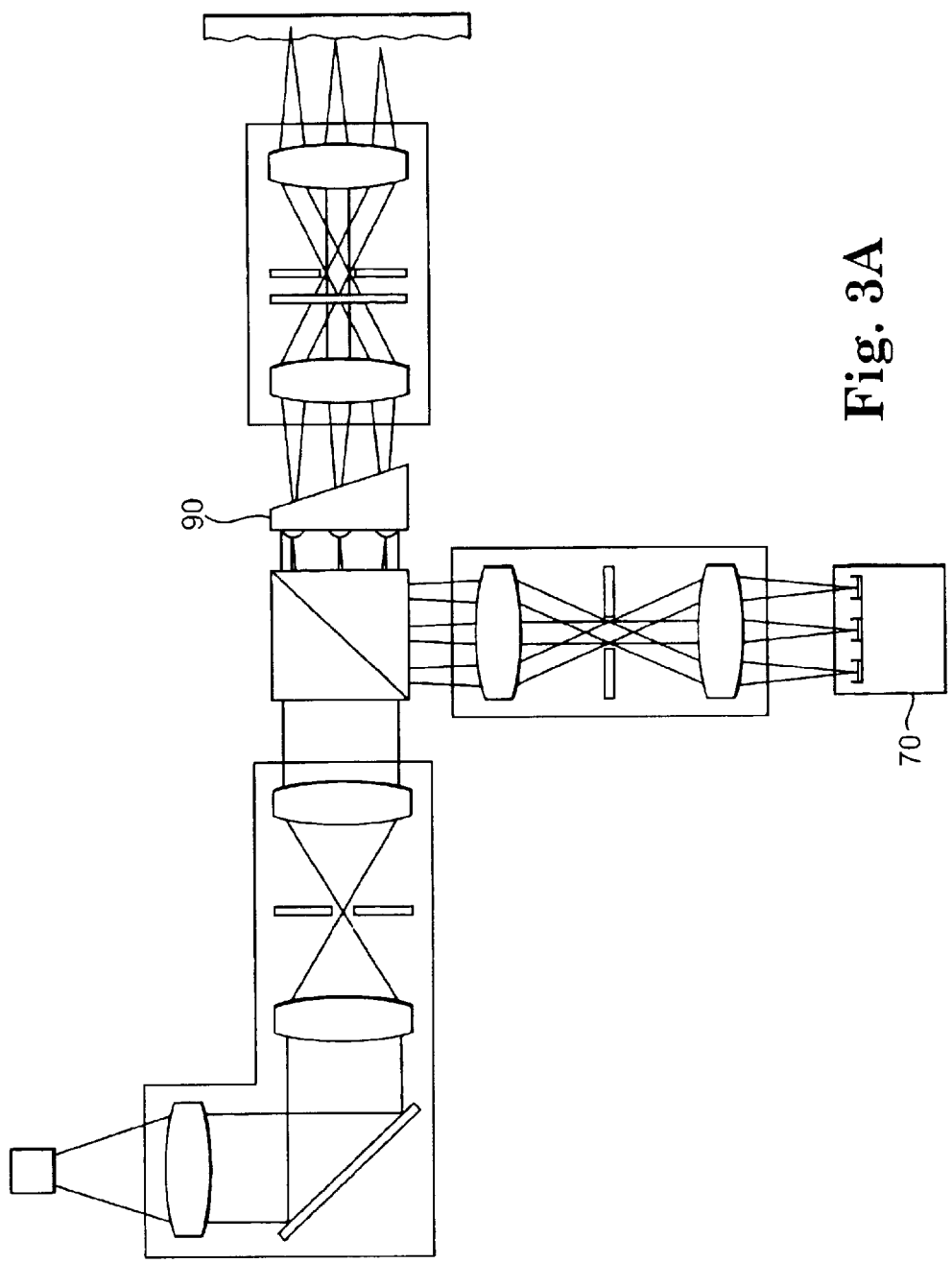

CONFOCAL 3D INSPECTION SYSTEM AND PROCESS

CROSS REFERENCE TO RELATED APPLICATIONS

This application cross references and incorporates by reference U.S. Provisional Patent Application No. 60/232,443 filed on Sep. 12, 2000.

BACKGROUND OF THE INVENTION

1. Technical Field

The present invention relates to a system, and process for use thereof, for inspecting wafers and other semiconductor substrates, and specifically for inspecting three dimensional (3D) features thereon such as bumps. Specifically, the present invention relates to a confocal optical system for inspecting bumps and other 3D features on wafers or like substrates, and a process of using such system.

2. Background Information

Over the past several decades, the semiconductor has exponentially grown in use and popularity. The semiconductor has in effect revolutionized society by introducing computers, electronic advances, and generally revolutionizing many previously difficult, expensive and/or time consuming mechanical processes into simplistic and quick electronic processes. This boom in semiconductors has been fueled by an insatiable desire by business and individuals for computers and electronics, and more particularly, faster, more advanced computers and electronics whether it be on an assembly line, on test equipment in a lab, on the personal computer at one's desk, or in the home via electronics and toys.

The manufacturers of semiconductors have made vast improvements in end product quality, speed and performance as well as in manufacturing process quality, speed and performance. However, there continues to be demand for faster, more reliable and higher performing semiconductors.

One process that has evolved over the past decade plus is the semiconductor inspection process. The merit in inspecting semiconductors throughout the manufacturing process is obvious in that bad wafers may be removed at the various steps rather than processed to completion only to find out a defect exists either by end inspection or by failure during use. In the beginning, wafers and like substrates were manually inspected such as by humans using microscopes. As the process has evolved, many different systems, devices, apparatus, and methods have been developed to automate this process such as the method developed by August Technology and disclosed in U.S. patent application Ser. No. 09/352,564. Many of these automated inspection systems, devices, apparatus, and methods focus on two dimensional inspection, that is inspection of wafers or substrates that are substantially or mostly planar in nature.

One rapidly growing area in the semiconductor industry is the use of bumps or other three dimensional (3D) features that protrude outward from the wafer or substrate. The manufacturers, processors, and users of such wafers or like substrates having bumps or other three dimensional desire to inspect these wafers or like substrates in the same or similar manner to the two dimensional substrates. However, many obstacles exist as the significant height of bumps or the like causes focusing problems, shadowing problems, and just general depth perception problems. Many of the current systems, devices, apparatus, and methods are either completely insufficient to handle these problems or cannot satisfy the speed, accuracy, and other requirements.

SUMMARY OF THE INVENTION

The inspecting of semiconductors or like substrates, and specifically the inspection of three dimensional features, such as bumps, on their surface is accomplished by the present invention, which is a confocal sensor system to improve depth response by eliminating out of focus light thereby resulting in the sensor producing a signal only when the surface being inspected is in a narrow focal range. The result is an accurate height determination for a given point or area being inspected such that the cumulation of a plurality of height determinations from use of the confocal sensor system across a large surface allows the user to determine the topography thereof.

In sum, this system and process creates multiple parallel confocal optical paths along a line whereby the out of focus light is eliminated by placing an aperture at a plane which is a conjugate focal plane to the surface of the sample. The result is that the sensor produces a signal only when the sample surface is in a narrow focal range.

BRIEF DESCRIPTION OF THE DRAWINGS

Preferred embodiment of the invention, illustrative of the best mode in which applicant has contemplated applying the principles, are set forth in the following description and are shown in the drawings and are particularly and distinctly pointed out and set forth in the appended claims.

FIG. 3A is a drawing of a second embodiment of the present invention;

Similar numerals refer to similar parts throughout the drawings.

DESCRIPTION OF THE PREFERRED EMBODIMENT

Figure 1:
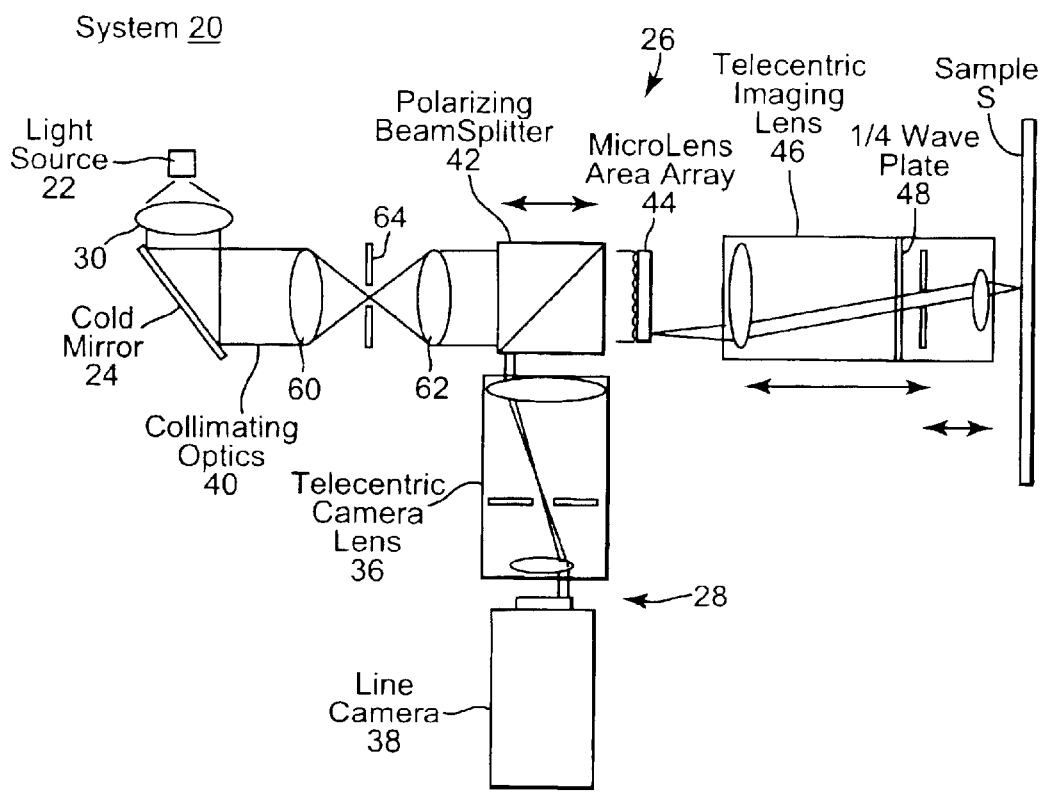
FIG. 1 is drawing of one embodiment of the present invention.

The three dimensional (3D) inspection system of the present invention is indicated generally at 20 as is best shown overall in FIG. 1 and is used in one environment to view, inspect, or otherwise optically observe three dimensional features, such as bumps, on an otherwise flat or planar substrate. The 3D inspection system includes a light source 22, a sensor system 26, and a camera system 28. It is also contemplated that in certain configurations a mirror 24 may be used.

The light source 22 is any source of light that provides sufficient illumination for the measurement system. Examples of the light source include, but are not limited to, white light sources such as halogen or arc lights, lasers, light emitting diodes (LEDs) including white LEDs or any of the various colored LEDs, fluorescent lights, or any other type of light source. In one embodiment as is shown in the Figures, the light source is preferably an arc lamp or halogen lamp.

The light source may be positioned in any position relative to the sensor so long as it provides the necessary light to the sensor 26 and sample S to be viewed, inspected or otherwise optically observed. In the embodiment shown in the Figures, the light source is offset, not axial, to the sensor system 26, and uses mirror 24 to orient the light in the desired axial direction within the sensor system 26. This offset light source 22 with mirror 24 is used because the mirror, which is a cold mirror, reflects visible light into the optics 30 as is needed and defined below while allowing undesirable infrared light to pass or transmit through the mirror and out of the system. Such undesirable infrared light is usually emitted from the light source and removed from the system by passing through the mirror. In the alternative, an infrared filter could be used to accomplish this task. Another alternative is a light source 22 could be used that emits only light in a controlled frequency, i.e. the visible frequency that is needed by the system and no other light, thereby eliminating the need to filter or reflect only desirable light. An example of this is a laser.

The light source 22 may include a reflector as is well known in the art to focus or direct the maximum light in the preferred direction.

In at least some embodiments, the system 20 further includes a lens or other optics 30 in between the light source 22 and the mirror 24, or if no mirror is needed then the sensor 26, for gathering or collecting maximum light from the light source 22 and directing it at the mirror 24 or sensor 26. The optics 30, in the embodiment shown, are a condenser lens located to collect light from the light source and direct it toward the mirror 24 or the sensor 26 if no mirror is used.

The light emitted from the light source 22 and directed by the mirror 24, if needed, enters sensor system 26 whereby it is manipulated, focused, split, reflected, refracted, collimated, recollimated, filtered, or otherwise processed and allowed to pass through if certain qualities or properties are met. The light that passes through the entire sensor system 26 is received by camera 28 and then processed by a computer or the like to calculate or determine the topography of the sample including the location, size, shape, contour, roughness, and/or metrology of the bumps or other features thereon.

The camera 28 may be any line scan camera, area scan camera, combination of multiple line scan cameras, time delay integration (TDI) line scan camera or other camera or cameras as one of skill in the art would recognize as functionally operational herewith. In the embodiment shown in FIG. 1, the camera 28 is a line scan camera. In the embodiment shown, the camera system 28 includes a telecentric camera lens 36 and a line camera 28.

In more detail and in the embodiment shown in the Figures, the sensor 26 includes collimating optics 40, an optional linear polarizer 41, a polarizing beam splitter 42, a microlens line array 44, a telecentric imaging lens 46, and a ¼ wave plate 48.

The collimating optics 40 may be any system or device that collimates light, that is makes the light rays from the light source 22 parallel to each other. The collimating optics 40 must collimate light from the light source into a high quality light beam. In the embodiment shown in the Figures, collimating optics 40 includes a pair of lenses 60 and 62 with a pin hole aperture 64 therebetween, all of which acts as a spatial filter. The overall function of this spatial filter is to remove noncollimated light by blocking it with the aperture. Lens 60 functions to direct and focus light toward aperture 64, whereby focused light passes through aperture 64 and is recollimated by lens 62.

An optional linear polarizer (not shown) is provided between the light source 22 and the polarizing beam splitter 42 to allow for light intensity control. Essentially all light not in line with the polarizer's preferential direction is blocked. This linear polarizer can be rotated relative to the polarizing beam slitter's polarization axis to provide light intensity control which is needed for sample to sample intensity control. Alternately, this linear polarizer provides additional polarization to the polarizing beam splitter 42 where and if one polarizing device is insufficient, that is not capable of providing 100% polarization, or where precaution is desired to make sure sufficient polarization occurs.

The collimated light enters the polarizing beam splitter 42. The polarizing beam splitter 42 may be any system or device that separates linear polarized light of one polarization from polarized light of the orthogonal polarization by transmitting one polarization and reflecting the orthogonal. In the embodiment shown in the Figures, the polarizing beam splitter 42 polarizes the collimated light transmitted from the collimating optics 40 and separates the linearly polarized light of one polarization from the orthogonally polarized light by allowing the transmission of the linearly polarized light while reflecting the orthogonally polarized light.

The linearly polarized light that transmitted through the polarized beam splitter 42 is directed at the microlens array 44 or other array structure such as a multiple microlens. The microlens line array 44 may be any system or device that orients collimated light into a controlled line or area array or like pattern.

Figure 2:
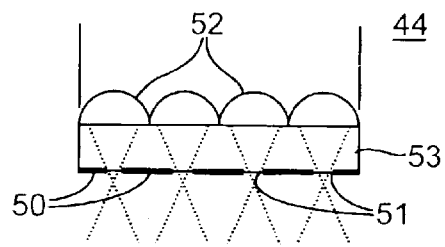
FIG. 2 is an illustration of the microlens portion of the present invention.

In the embodiment shown in the Figures, the microlens line array 44 is a line of microlenses. Each microlens has an opaque mask material deposited onto the back surface thereof. This opaque mask material 50 has small apertures 51 therein that are coincident to each microlens focal point and these small apertures 51 are sized to allow only the passage of light through the central lobe of the focal point of each microlens 52 as is illustrated in FIG. 2. In design, each microlens 52 in the array 44 is constructed such that the focal point of each microlens 52 in the array 44 corresponds to the thickness of the substrate 53 on which the microlenses are made.

Returning to FIG. 1, light passing through the aperture line formed by the multiple apertures aligned in the microlens array 44 is then collected by the telecentric imaging lens 46. The telecentric imaging lens 46 creates a reduced image of the pinhole array on the sample S surface.

The magnification of this telecentric lens is determined by the desired effective pixel size. For example, if the microlens diameter is 50 microns, and a micron pixel size is desired, the magnification for the telecentric imaging lens must be 0.1×.

This telecentric imaging lens 46 also contains the ¼ wave plate 48. This ¼ wave plate changes the polarization of the light passing through the telecentric lens 46 from linearly polarized to circularly polarized. This circularly polarized light is transmitted onto the sample S surface.

Light reflecting from the sample S surface incurs a phase change of 180 degrees. This phase change alters the circularly polarized light such that the reflected light is still circularly polarized, but in the opposite direction. This reflected light is returned back through the telecentric imaging lens 46 where the ¼ wave plate 48 changes the circularly polarized light back to linearly polarized light. However, the direction of the linear polarization is orthogonal to the original direction so as to cause it to be reflected by, not transmitted through, the polarizing beam splitter 42 as discussed below.

The light from the "in focus" portions of the sample S will pass back through the small apertures and be recollimated by the microlenses 44. All "out of focus" light will be blocked by the opaque mask around the apertures. The light which is passed back through the small apertures will now be reflected by the beam splitter 42 and then collected by the camera lens in the camera system 28.

This camera lens creates an image of the microlens array onto the camera sensor. The magnification of the camera lens is selected so that each microlens is imaged onto one sensor pixel. For example, if the microlens size is 50 microns, and the sensor pixel size is 10 microns, then the camera lens magnification must be 0.2×. The camera sensor is a linear photosensor with the number of pixels matching the number of microlenses.

Figure 3B:
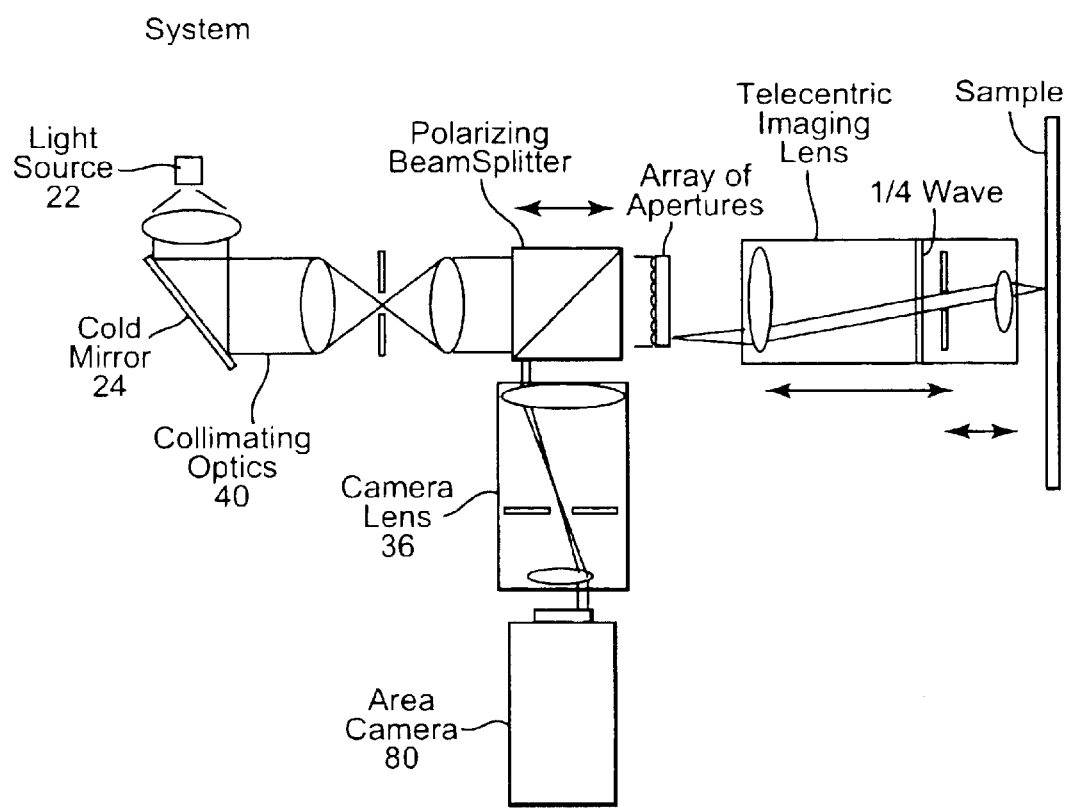
FIG. 3B is a drawing of another embodiment of the present invention.

In an alternative sensor arrangement, the camera may be multiple line cameras (shown at 70 in FIG. 3A) or an area camera (shown at 80 in FIG. 3B) used in multi-line mode. If such alternative embodiment is used, the microlens will consist of multiple linear arrays of lenses which focus light correspondingly onto the multiple array of linear photo sensors.

The scanning process for the above invention is as follows: The line of focal points or spots of the microlens array 44 will be oriented 90 degrees to the scanning direction. After the stage begins to move, the camera line starts integration at the rising edge of the scanning axis encoder clock. The stage moves distance of encoder counts equal to the horizontal optical size of the sensor. The camera ends integration on the falling edge of the last encoder count, transfers the data to a storage register, and begins the next integration period. For example, if the optical X-Y pixel size is 5 um, and the scanning axis encoder resolution is 50 nm, the camera is line triggered every 100 encoder counts to create square pixels. This line will then be scanned at a fixed height above the sample S surface either by moving the camera 28 or moving the sample S. This scan will generate one height location on a depth response curve for each pixel location on the sample S. The sensor will then return to its original starting position, be incremented in height, and the scan will be repeated to generate a second height location of the depth response curve for each pixel location on the sample S. This can then be repeated any number of times desired for the interpolation method used (typically at least two or three scans, although more are certainly contemplated and will assure accuracy). The multiple locations on the depth response curve are then interpolated for each pixel to generate a map of the surface height under the scan. The scans can then be repeated such that a height map is generated for the entire sample S surface.

The size of the "in focus" region is determined by the telecentric imaging lens 36. If this lens has a larger numerical aperture (~ratio of the focal length to diameter) the focus range will be small, and conversely if the lens 36 has a low numerical aperture the focus range will be large. The best "in focus" range is dependent on the height range that needs to be measured. The profile of each sensor element's response as the focus plane is translated through a sample surface is shown below:

The peak intensity of the profile corresponds to the location of the sample surface. Existing confocal microscopes can generate a 3D profile of a sample by stepping the sensor in very small increments of height, and storing the location of the maximum intensity. This is a slow process because many steps must be taken with very small step sizes to achieve high resolution and accuracy. The sensor of one embodiment of the present invention will not operate in the slow standard mode, but will take advantage of the fact that the depth profile remains constant for different sample types and light levels. Therefore, because the shape of the response can be known, it is possible to measure at only two or three height locations and accurately interpolate the location of the sample S surface.

As noted above, an alternative embodiment is contemplated using multiple lines of microlenses with either multiple line cameras or an area camera used in multiline mode. Each line of microlenses and its corresponding imaging camera or pixels serves as a separate confocal microscope. These microscopes are then adjusted such that each one has a different sample to sensor separation and therefore acquires confocal images at different heights. The sample to sensor separation may be adjusted by tilting the sample, by tilting the microlens array, or by placing glass plates or wedges (shown at 90 in FIG. 3A) between the microlens array and sample. These confocal microscopes running in parallel will acquire data at multiple heights, and therefore multiple locations on the depth response curves, during one acquisition of data. By measuring multiple locations on the depth response curve in a single scan, the overall speed of the system can be improved manyfold.

It is contemplated by the present invention that the sensor 26 ins a broader embodiment may be described as including the following: a collimating subsystem for making the light rays from the light source 22 parallel to each other, a desirable versus non-desirable light separator subsystem for separating the desired light from the non-desired light, a light gate subsystem for collecting light and only passing through to the sample S that light in focus, a filtering subsystem for filtering out non-focused light that reflects off of the sample S a light collector for collecting light that passed through the filtering subsystem, and an interpolator for gathering light intensity measurements taken at different heights from the light collector for a plurality of points and interpolating the measurements to define a topographic map of the sample S.

Figure 4:
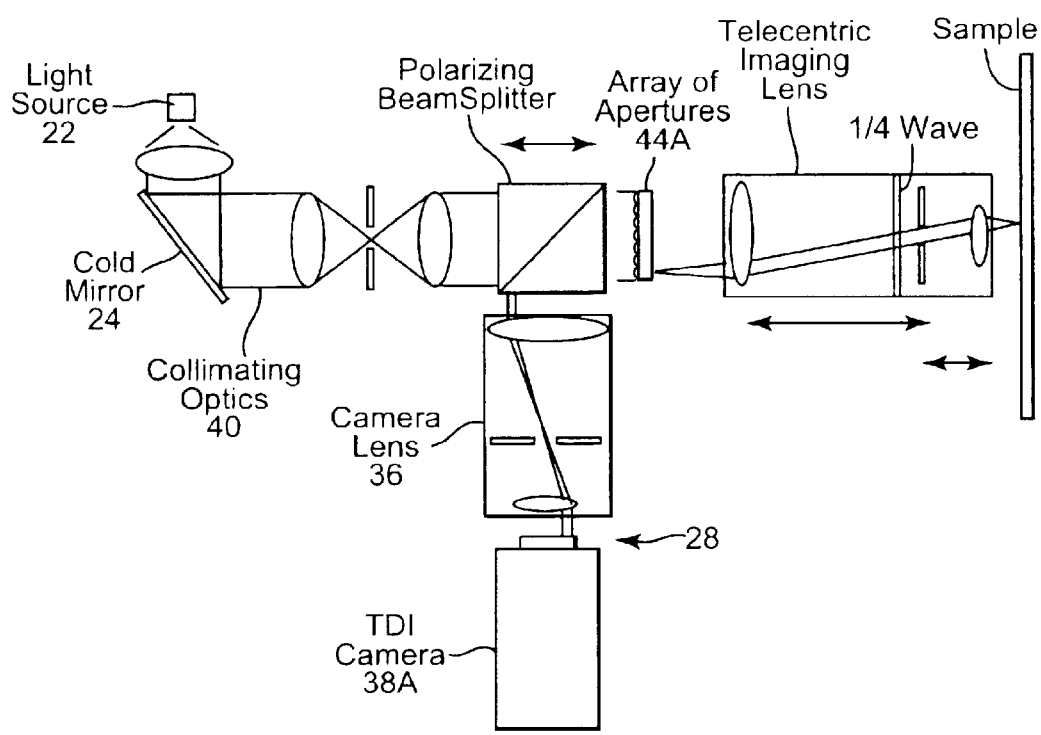
FIG. 4 is a drawing of another embodiment of the present invention.

Another-embodiment of the present invention is shown in FIG. 4 as system 20A. This embodiment is substantially similar to the first embodiment of FIGS. 1–2 as described above except the microlens array 44 of the first embodiment is replaced with an array of apertures or pinholes 44A and the camera system 28 includes a TDI camera 38A. It is also preferable that the light source 22 be a halogen light.

In sum, the present invention is a unique sensor and analysis technique which incorporates various novel, useful and nonobvious inventions including using a line-scan camera in conjuction with multiple, parallel confocal apertures, lenses, microscopes or other arrays of specially designed light passages to quickly acquire area confocal images at a particular sample/sensor separation and then, by using interpolation of multiple images at several sample/sensor separations, estimating the height of certain features.

Accordingly, the invention as described above and understood by one of skill in the art is simplified, provides an effective, safe, inexpensive, and efficient device, system and process which achieves all the enumerated objectives, provides for eliminating difficulties encountered with prior devices, systems and processes, and solves problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the invention's description and illustration is by way of example, and the invention's scope is not limited to the exact details shown or described.

Having now described the features, discoveries and principles of the invention, the manner in which it is constructed and used, the characteristics of the construction, and the advantageous, new and useful results obtained; the new and useful structures, devices, elements, arrangements, parts and combinations, are set forth in the appended claims.

We claim:

1. An inspection device including:
   a collimating light source;
   an array of apertures for receiving light generated by the light source and orienting the light into a controlled point, line or area array or like pattern;
   means for creating a reduced image of a pinhole array on a sample surface; and
   multiple line scan cameras for collecting focused light reflected from the sample surface.

2. The inspection device of claim 1 wherein the array of apertures is a microlens array.

3. The inspection device of claim 1 wherein the array of apertures is a line of microlenses.

4. The inspection device of claim 1 wherein the multiple line scan cameras includes a TDI camera.

5. The inspection device of claim 1 wherein the collimating light source is an illumination source and collimating optics.

6. The inspection device of claim 5 wherein the illumination source is a halogen lamp.

7. The inspection device of claim 5 wherein the illumination source is a laser.

8. The inspection device of claim 5 wherein the illumination source is a light emitting diode.

9. The inspection device of claim 5 wherein the collimating optics includes a spatial filter.

10. The inspection device of claim 5 wherein the collimating optics includes a pair of lenses with a pinhole aperture therebetween.

11. The inspection device of claim 1 wherein the means for creating a reduced image of a pinhole array on a sample surface includes a telecentric imaging lens.

12. The inspection device of claim 1, further comprising a wedge between the array of apertures and the sample surface.

13. The inspection device of claim 1, wherein the inspection device is configured to scan horizontally across the sample surface.

14. The inspection device of claim 1, wherein the inspection device is configured to scan laterally across the sample surface.

15. The inspection device of claim 1, wherein the inspection device is configured to horizontally scan the reduced image of a pinhole array across the sample surface.

16. The inspection device of claim 1, wherein the inspection device is configured to laterally scan the reduced image of a pinhole array across the sample surface.

17. An inspection device including:
   a light source;
   collimating optics for receiving light from the light source and collimating the light;
   a polarizing beam splitter for separating linear light from orthogonally polarized light by polarizing the collimated light received from the collimating optics;
   a microlens array for receiving the linearly polarized light from the polarizing beam splitter and orienting the light into a controlled point, line or area array or like pattern;
   a telecentric imaging lens including a ¼ wave plate for collecting the oriented linearly polarized light, changing the polarization of this light from linear to circular, and creating a reduced image of a pinhole array on a sample surface; and
   a TDI camera for collecting focused light reflected from the sample surface after it has been polarized as it passes back through the ¼ wave plate, recollimated by the microlenses and separated from any non-focused light, and reflected by the polarizing beam splitter to the camera.

18. The inspection device of claim 17 wherein the light source is selected from the following group: halogen light, laser, light emitting diode, and fluorescent lights.

19. An inspection device including:
   a light source;
   collimating optics for receiving light from the light source and collimating the light;
   a polarizing beam splitter for separating linear light from orthogonally polarized light by polarizing the collimated light received from the collimating optics;
   an array of apertures for receiving the linearly polarized light from the polarizing beam splitter and orienting the light into a controlled point, line or area array or like pattern;
   telecentric imaging lens including a ¼ wave plate for collecting the oriented linearly polarized light, changing the polarization of this light from linear to circular, and creating a reduced image of a pinhole array on a sample surface; and
   a TDI camera for collecting focused light reflected from the sample surface after it has been polarized as it passes back through the ¼ wave plate, recollimated by the array of apertures and separated from any non-focused light, and reflected by the polarizing beam splitter to the camera.

* * * * *